United States Patent [19]

van Nassau et al.

[11] 4,410,503
[45] Oct. 18, 1983

[54] PROCESS FOR THE REMOVAL OF UREA, AMMONIA, AND CARBON DIOXIDE FROM DILUTE AQUEOUS SOLUTIONS

[75] Inventors: Petrus J. M. van Nassau, Sittard; Adolphe M. Douwes, Geleen, both of Netherlands

[73] Assignee: Unie Van Kunst-Mestfabrieken, Maliebaan, Netherlands

[21] Appl. No.: 353,385

[22] Filed: Mar. 1, 1982

[30] Foreign Application Priority Data

Feb. 28, 1981 [NL] Netherlands ................. 8100989

[51] Int. Cl.³ ................................. C01C 1/04
[52] U.S. Cl. ........................... 423/359; 203/11; 564/69
[58] Field of Search ............... 423/359; 203/11; 564/69

[56] References Cited

U.S. PATENT DOCUMENTS

| | | | |
|---|---|---|---|
| 3,361,534 | 1/1968 | Johnson et al. | 423/653 |
| 3,922,222 | 11/1975 | Van Moorsel | 203/11 |
| 4,260,461 | 4/1981 | Pottharst | 203/11 |
| 4,260,462 | 4/1981 | Didycz et al. | 203/11 |
| 4,327,068 | 4/1982 | Lagana et al. | 423/359 |

Primary Examiner—O. R. Vertiz
Assistant Examiner—Wayne A. Langel

[57] ABSTRACT

An improved process for the removal of urea, ammonia, and carbon dioxide from process condensate derived from coupled urea and ammonia syntheses by hydrolysis of urea and desorption of ammonia and carbon dioxide. Process condensate poor with respect to ammonia is treated at a pressure of between about 15 and 42 bar and a temperature of between about 200° C. and 320° C. in a reaction column with steam to form a gas mixture containing ammonia, carbon dioxide, and water vapor, and an aqueous liquid virtually free of urea, ammonia, and carbon dioxide.

11 Claims, 2 Drawing Figures

PROCESS FOR THE REMOVAL OF UREA, AMMONIA, AND CARBON DIOXIDE FROM DILUTE AQUEOUS SOLUTIONS

BACKGROUND OF THE INVENTION

The present invention relates to an improved process for the removal of urea, ammonia, and carbon dioxide from dilute aqueous solutions obtained as process condensate from coupled ammonia and urea syntheses.

In the preparation of ammonia from hydrocarbons, primarily methane, a synthesis gas is first prepared in a primary reformer by reacting the hydrocarbon with an excess of steam, generally according to the reaction equation $CH_4 + H_2O \rightarrow CO + H_2$. Subsequently, the gas mixture leaving the primary reformer is introduced into a secondary reformer together with air in order to further convert any hydrocarbon present with oxygen, and, moreover, to introduce the nitrogen required for the ammonia synthesis.

The gas mixture leaving the secondary reformer mainly consists of water vapor, carbon dioxide, nitrogen, carbon monoxide, and hydrogen. This mixture is treated catalytically to convert the carbon monoxide, generally according to the reaction equation $CO + H_2O \rightarrow CO_2 + H_2$, so that a gas mixture of carbon dioxide, nitrogen, hydrogen, water vapor, and small quantities of carbon monoxide is obtained. The excess water vapor in this mixture is condensed and forms the so-called process condensate. The carbon dioxide is removed from this gas mixture by washing, and the small quantity of carbon monoxide remaining is converted in a methanator into methane, which is not poisonous to the ammonia synthesis catalyst. The resulting gas mixture containing primarily nitrogen and hydrogen is a suitable starting mixture for the ammonia synthesis.

During the various processing steps, small quantities of by-products are also formed, such as ammonia in the secondary reformer, and methanol, methylamine, and other organic impurities in the carbon monoxide conversion. When the excess water vapor is condensed, these by-products will enter the process condensate. The process condensate additionally will contain dissolved carbon dioxide and traces of metal compounds originating from the catalysts and the equipment.

The presence of these impurities in the process condensate is undesirable, whether the process condensate is to be fed back into the system as boiler feed water, or whether it is to be discharged to the environment as waste water.

The quantity of process condensate resulting from an ammonia plant depends on the steam/hydrocarbon ratio in the primary reformer and, when considered together with the small quantities of condensate from the coolers of the synthesis gas compressor, and condensate obtained in the methanator, amounts to about 1.1 to 1.25 tons per ton of ammonia produced. This condensate as a rule contains about 0.08 to 0.1 percent by weight ammonia, 0.15 to 0.2 percent by weight carbon dioxide, 0.1 to 0.2 percent by weight methanol, 30 to 50 ppm organic impurities and traces of the metals iron, copper, zinc, aluminum, sodium, and calcium.

In the preparation of urea from ammonia and carbon dioxide, a urea synthesis solution, still containing a substantial quantity of free ammonia and non-converted ammonium carbamate, is formed at elevated temperature and pressure. The carbamate is thereafter decomposed in one or more steps into ammonia and carbon dioxide. This ammonia and carbon dioxide are driven out of the urea solution together with the free ammonia present, and are usually recirculated to the urea synthesis reactor. In the final carbamate decomposition step, the aqueous urea solution obtained still contains some quantities of dissolved ammonia and carbon dioxide, and these are substantially removed by expansion to atmospheric or lower pressure. The resulting aqueous urea solution is concentrated by evaporation and/or crystallization and further processed.

During this evaporation process, a gas mixture is formed containing, in addition to water vapor, ammonia and carbon dioxide, together with entrained fine droplets of urea. This gas mixture, as well as the gas mixture separated off during the expansion of the urea solution after the final decomposition step, is condensed to form process condensate. The process condensate thus obtained is in part fed back into the urea process to absorb the gas mixture separated out in the final decomposition step. The remaining portion of this condensate is generally discharged from the process.

The process condensate from a urea synthesis plant also includes the water fed into the process as steam for operating the ejectors in the evaporation and/or crystallization section, washing water, flushing water to the stuffing boxes of the carbamate pumps, and the like. In addition, one mole of water is formed for each mole of urea produced. Thus, in a urea plant having a capacity of 1900 tons of urea per day, 570 tons of water is formed, and in addition thereto, depending on the temperature of the cooling water used in the process, about 380–600 tons of water per day is fed into the process, so that approximately 950–1170 tons of water in total must be removed from the process per day.

This process condensate resulting from a urea synthesis process generally contains about 2 to 9 percent by weight ammonia, 0.8 to 6 percent by weight carbon dioxide, and 0.3 to 1.5 percent by weight urea. To simply discharge these materials from the process represents, on one hand, a loss of substantial quantity of raw materials. On the other hand, this represents a substantial load to the surface waters into which this waste water would be discharged, and is no longer permitted in many countries.

Consequently, in coupled installations for the preparation of both ammonia and urea, large quantities of process condensate are formed in each installation, which vary greatly in composition, and which can be discharged to the environment, or used as boiler feed water, only after careful purification.

In Industrial Wastes, September/October 1976, pages 44–47, a process is described, wherein process condensate obtained in a urea synthesis plant, which has already been freed from a portion of its ammonia and carbon dioxide at a low pressure, is passed, at a higher pressure, into the bottom of a reaction column. In the reaction column it is heated by steam so as to hydrolyze the urea present. Thereafter, the resulting solution of reduced urea content is expanded and stripped with steam in a desorption zone. This method, wherein the solution being processed flows cocurrently with the steam and the gaseous ammonia and carbon dioxide, has the drawback that even after a long residence time of the solution in the reaction column, the final urea and ammonia content is relatively high.

It has previously been suggested in Netherlands patent application No. 7705356 that superheated steam be formed from the process condensates obtained from ammonia and urea synthesis processes. To accomplish this, the process condensate obtained in the urea preparation is first fed into a hydrolyzing column wherein the urea is hydrolyzed. The ammonia and carbon dioxide formed by the hydrolysis are then desorbed in a desorption column, and the remaining solution, together with the process condensate obtained from the ammonia preparation, is converted into superheated steam. This superheated steam is then fed to the primary reformer in the ammonia synthesis process. Optionally, some of the ammonia and carbon dioxide can be removed from the combined process condensate by expansion and stripping off the gases liberated in this process, prior to converting the condensate into superheated steam.

The disadvantage of the above-described process is that the presence of ammonia near equilibrium conditions impedes the hyrolysis of the urea such that the final concentration of urea is higher than it would be in the absence of ammonia. This incomplete hydrolysis of urea presents a real danger in that, when urea-containing process condensate is converted into steam, the urea in the steam boiler will decompose into ammonia and carbon dioxide and present a significant risk of corrosion.

SUMMARY OF THE INVENTION

It is the object of the present invention to provide an improved process by which process condensates obtained from coupled ammonia and urea syntheses can be treated together so as to render them suitable either for discharge to the environment or use as boiler feed water, without the above-noted disadvantages. This is accomplished by feeding a urea-containing process condensate, relatively poor in ammonia, into the upper portion of a reaction column wherein it is heated and stripped by means of steam fed into the bottom of the column. The temperature and pressure in the column is maintained such that urea is decomposed therein into ammonia and carbon dioxide. The steam serves not only as a heating agent, but also as a stripping agent.

Another object of the present invention is to provide an improved process wherein a more efficient use may be made of the steam to be supplied to the primery reforming step than in the known coupled processes for the synthesis of ammonia and urea.

The invention, therefore, relates to an improved process for the removal of urea, ammonia, and carbon dioxide from dilute aqueous solutions obtained as process condensates in coupled ammonia and urea syntheses by hydrolysis of urea and desorption of ammonia and carbon dioxide. Specifically, the process condensate, which is poor with respect to ammonia, is treated with steam in a reaction column at a pressure of between about 15 and 42 bar and at a temperature of between about 200° and 320° C. The resulting gas mixture containing ammonia, carbon dioxide, and water vapor, is removed from the top portion of the column, and an aqueous liquid virtually free of urea, ammonia and carbon dioxide is removed from the bottom of the column. Preferably, the reaction column is operated at a pressure of between about 32 and 40 bar, and at a temperature of between about 220° C. and 280° C. in order to insure that virtually complete hydrolysis of the urea takes place in a relatively short time. By utilizing the improved process, it is possible to reduce the urea concentration in the process condensate down to a level of 10 ppm or lower.

The water vapor contaminated with ammonia and carbon dioxide, which is discharged from the top portion of the reaction column, may be used directly as reforming steam in the primary reformer of the ammoniaplant to convert gaseous hydrocarbons, e.g. methane, into carbon monoxide and hydrogen. Thus, this steam performs two functions i.e., it acts as a heating and a stripping agent in the reaction column and it acts as reforming steam in the manufacture of the synthesis gas.

The process condensate from the urea synthesis contains a relatively larger amount of ammonia than the process condensate which is poor with respect to ammonia, a portion of the ammonia and carbon dioxide is first removed from the urea synthesis condensate by a desorption column prior to treatment in the reaction column. Preferably as much ammonia and carbon dioxide as possible is removed in the desorption column. This desorption column is operated at a pressure of between about 1 and 5 bar, using steam having a pressure of between 1 and 5 bar as both the heating and stripping agent.

The resulting gas mixture obtained from the top of the desorption column is at least partially condensed, and a portion of the condensate thus formed is returned as reflux. The major portion of this condensate, together with any non-condensed portion of the gas mixture, is supplied to the low-pressure carbamate condensor in the urea synthesis process. It is also possible to supply the gas mixture obtained from the top of the desorption column to the low-pressure carbamate condenser of the urea synthesis process without prior condensation.

The term 'poor with respect to ammonia' as used herein shall be understood to mean that the amount of ammonia present in the urea-containing solution is so low that in the bottom part of the reaction column where the urea concentrations are very low further hydrolysis of urea will not be hampered. Generally, ammonia and carbon dioxide should be removed from the process condensate in the desorption column to such an extent that the feed to the reaction column contains less than about 1 percent by weight of ammonia. Very low urea and ammonia contents can be attained with feeds to the reaction column containing 0.3 percent by weight or less of ammonia. Then a virtually complete hydrolysis of the urea is obtained in a relatively short time. As the amount of ammonia present in the feed to the reaction column increases a longer residence time is required for a virtually complete hydrolysis of the urea.

The low-ammonia process condensates from the ammonia and the urea synthesis processes can be fed to the reaction column either separately or as a single flow.

In one embodiment of the present process, the urea in the process condensate can be partially hydrolyzed in a separate heating zone. This hydrolysis can be effected by passing the low-ammonia process condensate removed from the bottom of the desorption column through a residence zone prior to feeding it to the reaction column. The separate residence zone can be formed, for instance, by a simple wide tube provided with means to supply heat for maintaining the temperature at the required level and, if desired, to supply further heat for hydrolyzing part of the urea. The heat may be directly supplied by introducing live steam or it may be indirectly supplied through a steam jacket or electric heating coils. If desired, this wide tube heating means can be placed inside the reaction column in such a manner that the low-ammonia process condensate flows up through the tube and through an overflow into the top of the reaction column. In this manner, the heating and pre-hydrolysis of urea can be effected by transferring heat from the steam fed into the reaction column through the wall of the tube. In this embodiment the wall thickness of the tube may be small because the pressures inside and outside the tube are virtually the same.

In another embodiment of the process of the present invention, a portion of the mixture from the upper part of the reaction column is removed to a heating zone, heated and returned back into the reaction column at a level below the level at which it was removed from the column.

Although both of these embodiments discussed above require an additional zone, savings may be realized because part of the time needed for hydrolysing the urea is now obtained by retaining the condensate for some time in an apparatus of very simple design and as a result the reaction column may be of smaller dimensions.

Steam, having a pressure of about 15 to 42 bar is preferably utilized as the heating and stripping agent in the reaction column. Preferably, the steam to be supplied to the primary reformer is used to this end. It is also possible, however, to use other inert gases, but they must be separated off again, which involves extra costs.

DETAILED DESCRIPTION OF THE INVENTION

The improvement of this invention will be illustrated by means of the figures and the following description.

Figure 1:
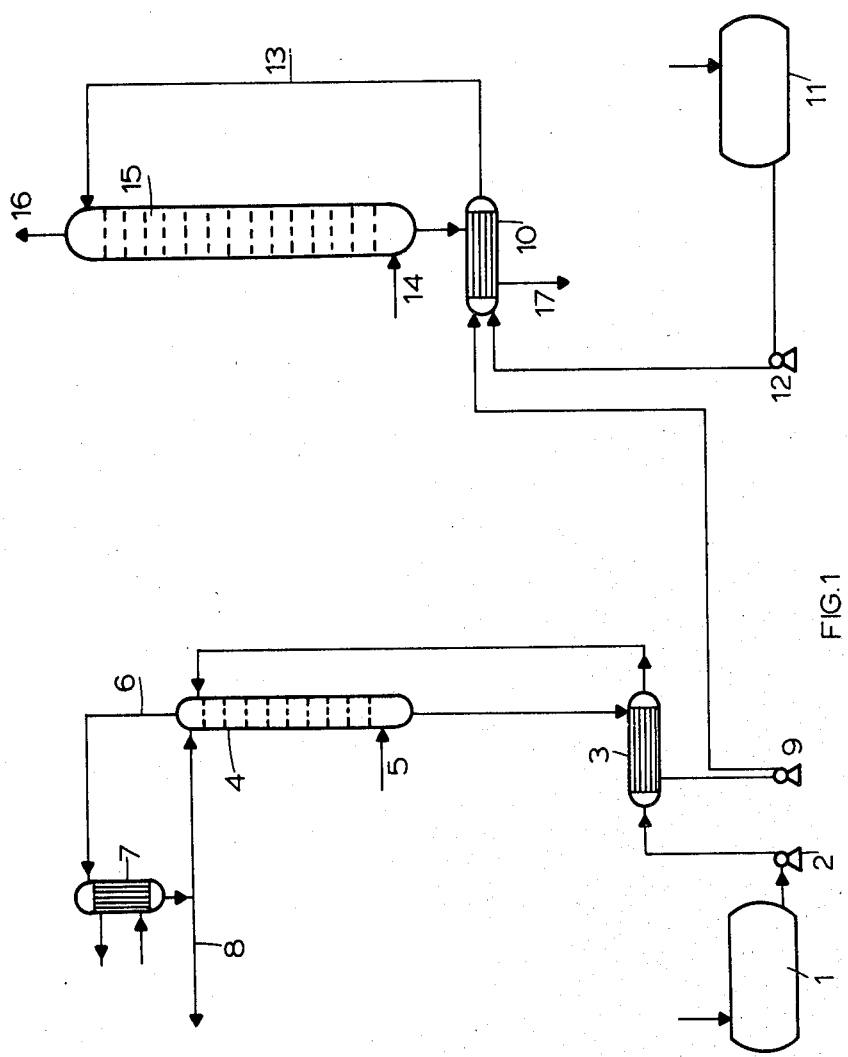

In applying the process according to FIG. 1, the process condensate from the urea synthesis, collected in tank 1, is brought up to a pressure of 1-5 bar by means of pump 2 and fed, via heat exchanger 3, into desorption column 4. In column 4, a major portion of the dissolved ammonia and carbon dioxide is driven out by the stripping action and heat content of low-pressure steam fed through line 5 into the lower half of column 4.

The resulting gas mixture containing ammonia, carbon dioxide, and a quantity of water vapor, is removed through line 6, and is completely condensed in reflux condenser 7. A small portion of the condensate is returned to the top of desorption column 4, and the major portion is supplied through line 8 to the urea synthesis, for instance, to the condensation and absorption zone of the final carbamate decomposition step.

The solution treated in desorption column 4 and still containing, in addition to small quantities of ammonia and carbon dioxide, virtually the entire quantity of urea originally present, is subsequently increased in pressure to 15-42 bar by means of pump 9, and fed into the top of reaction column 15 via heat exchanger 10 and line 13.

The process condensate from the ammonia synthesis, collected in tank 11, is brought up to the reaction column pressure by pump 12, and is fed also via heat exchanger 10 and line 13 into the top of reaction column 15, together with the process condensate from the urea synthesis.

Reaction column 15 is divided by, for instance, perforated plates with overflow weirs into a number of compartments serving as ideal gas bubble contactors. Steam at a pressure of from about 15 to 42 bar is fed into the bottom of this reaction column through line 14. The temperature in the column is controlled by metering the quantity of steam and the pressure in the reaction column. The steam supplies the heat required both for the decomposition of carbamate formed by hydrolysis of urea, and for the evaporation of the ammonia and carbon dioxide thus formed and at the same time acts as a stripping agent. It is supplied in such a quantity that the concentration of ammonia and carbon dioxide in the bottom solution of the reaction column is below the limit set, e.g. below 10 ppm and no subsequent desorption step for removing further quantities of ammonia and carbon dioxide is necessary.

The urea content of the solution decreases fairly rapidly as it flows down reaction column 15, decreasing more rapidly at higher temperatures. It has been found that the determining factor of the final urea content, after a certain residence time, is the concentration of ammonia and carbon dioxide in the liquid. For this reason, the pre-desorption of ammonia and carbon dioxide is often necessary to reach the required low urea content of 10 ppm or lower. For instance, at an average temperature of 245° C. in the reaction column, a minimum residence time of about 5-10 minutes is required. As the average temperature in the reaction column is higher, a shorter residence time will suffice.

The mixture of gases driven off and steam formed in reaction column 15 is removed from the top portion of the column and fed, through line 16, to a primary steam reformer (not illustrated) for the preparation of synthesis gas. The ammonia, methanol, and other organic components present in the gas mixture are broken down in the primary reformer.

An aqueous liquid stream containing urea and ammonia in concentrations of 10 ppm or lower, depending on the quantity of steam, is removed from the bottom of reaction column 15. The heat from this stream is used in heat exchanger 10 to heat the feed to reaction column 15, and is subsequently either fed, through line 17, to a device (not illustrated) for the removal of metal compounds and for the preparation of boiler feed water, or is discharged in whole or in part from the process.

Figure 2:
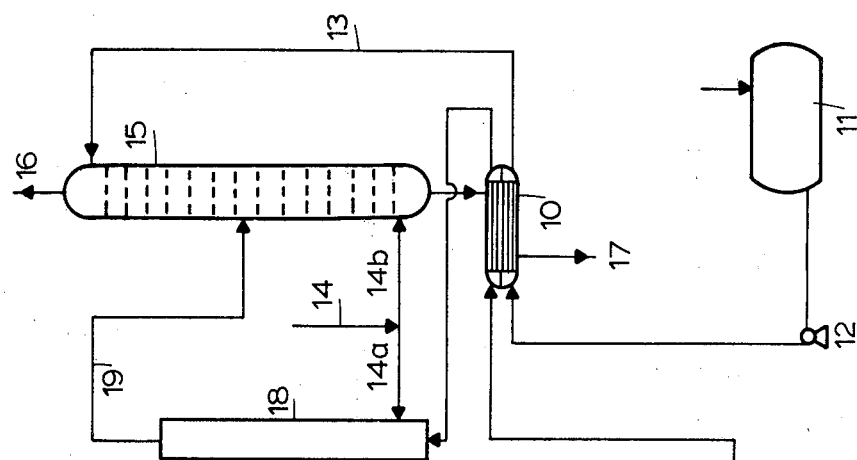
Figure 2:
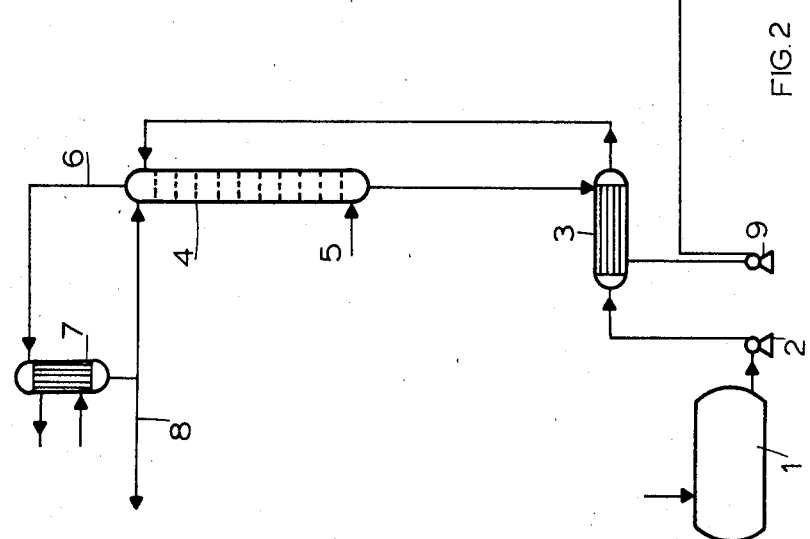

In applying the process according to FIG. 2, the process condensate from the urea synthesis, after removal of as much ammonia and carbon dioxide as possible in desorption column 4, is passed through heating zone 18 prior to the treatment in the reaction column in order to pre-hydrolyze a portion of the urea. The low-ammonia process condensate is brought by pump 9 up to a pressure of 15-42 bar and fed via heat exchanger 10 into heating zone 18. The vapor-liquid mixture formed in heating zone 18 is removed from the top thereof and fed, through line 19, into the top of reaction column 15. A portion of the steam supplied through line 14 is fed to heating zone 18 through line 14a as live steam, and the remaining steam if fed through line 14b into reaction column 15 wherein it is used to decompose the urea and drive off the ammonia and carbon dioxide thus formed. The process condensate from the ammonia synthesis is separately fed, via pump 12, through a separate portion of heat exchanger 10 and line 13, into the top of reaction column 15.

Preferred embodiments of the improvement process will be illustrated by means of the following examples.

EXAMPLE 1

By means of the process configuration shown in FIG. 1, process condensate was treated which had been obtained from a urea plant having an output of 1900 tons per day, and from an ammonia plant which was coupled to the urea plant, having an output of 1130 tons per day. All quantities are given in kg/hour.

The process condensate from the urea plant, totaling 48,345 kg, containing 778 kg urea, 1554 kg $NH_3$, 878 kg $CO_2$, and 45,135 kg water, was heated in heat exchanger 3 from a temperature of 40° C. up to 80° C. In desorption column 4, this solution was made to flow, at pressure of 4 bar, countercurrently against 9800 kg steam having a temperature of 143° C. and a pressure of 4.5 bar. From the top of desorption column 4, a gas mixture was removed having a composition of 2008 kg $NH_3$, 1114 kg $CO_2$, and 2102 kg $H_2O$. This gas mixture was completely condensed, and a portion of the solution thus obtained, having a temperature of 45° C. and consisting of 463 kg $NH_3$, 263 kg $CO_2$, and 485 kg $H_2O$, was returned as reflux to desorption column 4. The remaining portion of this solution was returned to the urea plant. The solution leaving the bottom of desorption column 4 contained 9 kg $NH_3$, 778 kg urea, and 53,318 kg $H_2O$, and had a temperature of 100° C. This solution was brought up to a pressure of 38 bar by means of pump 9.

The process condensate from the ammonia plant, totaling 52,400 kg, contained 60 kg $NH_3$, 190 kg $CO_2$, and 110 kg $CH_3OH$, and 52,040 kg $H_2O$, had a temperature of 50° C. and was brought up to a pressure of 38 bar by means of pump 12. This process condensate was then heated, together with the process condensate from the urea plant, to 240° C. in heat exchanger 10 and fed into the top of reaction column 15. The quantity of steam fed into the bottom of this reaction column was 40,000 kg, and it had a temperature of 352° C. and a pressure of 38 bar.

The flow rate in the reaction column was regulated so that the residence time of the liquid in the column was 5–10 minutes. The urea present in the feed was virtually completely hydrolyzed to form $NH_3$ and $CO_2$, and 30,620 kg of a gas mixture, having a temperature of 242° C. and a pressure of 37 bar, was removed from the top of the reaction column. This gas mixture, containing 95.5 percent $H_2O$, 1.6 percent $NH_3$, 2.5 percent $CO_2$, and 0.35 percent $CH_3OH$, was fed to the primary reformer of the ammonia plant. The bottom product of the reaction column, consisting of 115,885 kg water and having 10 ppm $NH_3$, 5 ppm urea, 25 ppm methanol, and traces of heavy metals, was used for pre-heating the feed to the reaction column, causing its temperature to fall from 246° C. to 106° C. This aqueous liquid was subsequently fed through line 17 to the boiler feed water system.

EXAMPLE 2

By means of the process illustrated in FIG. 2, the same quantities of process condensate from the urea plant and ammonia plant as described in Example 1 were processed. The treatment of the process condensate of the urea plant in desorption column 4 was carried out in the same way as described in Example 1. Via pump 9, 54,105 kg of the urea process condensate, now having a reduced $NH_3$ content, was fed at a pressure of 38 bar and a temperature of 100° C., into heating zone 18. This condensate had a composition of 53,318 kg $H_2O$, 9 kg $NH_3$, and 778 kg urea. Into this heating zone, 12,000 kg of steam with a temperature of 352° C. and a pressure of 38 bar was fed to line 14a. From the top of heating zone 18, 66,105 kg of a liquid-vapor mixture, having a composition of 65,108 kg $H_2O$, 406 kg $NH_3$, 513 kg $CO_2$, and 78 kg urea, was removed. The flow rate was regulated so that the residence time in heating zone 18 was about 8 minutes. The liquid-vapor mixture removed from the top of heating zone 18 was fed into the reaction column through line 19 and was therein contacted with 28,000 kg steam. This steam, having a temperature of 352° C. and a pressure of 38 bar, was supplied through 14b. The quantities of vapor and liquid carried off from the reaction column, and their compositions, correspond to those described in Example 1. However, the effective volume of the reaction column is about 10% smaller than in the process of Example 1.

What is claimed is:

1. In a coupled process comprising an ammonia synthesis zone having a primary reformer in which a hydrocarbon gas is reacted with steam to form a synthesis gas, and a urea synthesis zone, wherein process condensate comprised of a dilute aqueous solution of ammonia and carbon dioxide obtained from said ammonia synthesis zone, and process condensate comprised of a dilute aqueous solution of urea, ammonia, and carbon dioxide from said urea synthesis zone, are treated to remove at least a portion of said urea, carbon dioxide, and ammonia therefrom by hydrolysis of said urea and desorption of ammonia and carbon dioxide, the improvement comprising:

introducing said urea synthesis zone process condensate into a desorption zone wherein at least a portion of said ammonia and carbon dioxide are removed as a gas mixture from said urea synthesis zone process condensate at a pressure of between about 1 and 5 bar so as to render it poor with respect to ammonia;

introducing said urea synthesis zone process condensate poor with respect to ammonia, and said ammonia synthesis zone process condensate, into a reaction column wherein said combined condensates are treated with steam at a pressure of between about 15 and 42 bar, and at a temperature of between about 200° C. and 320° C.;

removing from the bottom portion of said reaction column an aqueous liquid virtually free of urea, ammonia, and carbon dioxide; and removing from the top portion of said reaction column a gas mixture containing ammonia, carbon dioxide, and water vapor, and introducing said gas mixture into said primary reformer as at least a part of said steam reacted to form said synthesis gas.

2. The process of claim 1 wherein said treatment is carried out at a pressure of between about 32 and 40 bar, and at a temperature of between about 220° C. and 280° C.

3. The process of claim 1 wherein said the process condensate introduced into said reaction column has an ammonia concentration of less than 1 percent by weight.

4. The process of claim 1 wherein the process condensate introduced into said reaction column has an ammonia concentration of less than 0.3 percent by weight.

5. The process of claim 1 wherein in at least a portion of the urea present in said urea synthesis zone process condensate poor with respect to ammonia is hydrolyzed in a separate residence step prior to treating said urea synthesis zone process condensate in said reaction column.

6. The process of claim 5 wherein said separate step is carried out in a separate heating zone within said reaction column.

7. The process of claim 1 wherein a portion of the aqueous liquid is removed from the upper portion of said reaction column, passed through a separate residence zone, and returned to said reaction zone at a level below the level at which it is removed.

8. The process of claim 1 wherein the steam used for said treatment within said reaction column has a pressure of between about 15 and 42 bar.

9. The process of claim 1 wherein said aqueous liquid removed from the bottom portion of said reaction column is used as boiler feed water.

10. The process of claim 1 wherein said process condensate introduced into said reaction column is preheated by heat exchange with the aqueous liquid removed from the bottom portion of said reaction column.

11. The process of claim 10 wherein said gas mixture containing ammonia and carbon dioxide from said desorption column is at least partially condensed, and a portion of the dilute aqueous solution containing ammonia and carbon dioxide thus obtained is returned as reflux to said desorption column, and the remaining portion of said solution, together with any non-condensed portion of said gas mixture, is fed to the low pressure carbamate condenser of said urea synthesis zone.

* * * * *